(12) United States Patent
Tuval et al.

(10) Patent No.: US 9,764,113 B2
(45) Date of Patent: Sep. 19, 2017

(54) CURVED CATHETER

(71) Applicant: MAGENTA MEDICAL LTD, Kadima (IL)

(72) Inventors: Yosi Tuval, Even Yehuda (IL); Ehud Schwammenthal, Raanana (IL); Daniel Glozman, Kefar Adummim (IL)

(73) Assignee: MAGENTA MEDICAL LTD, Kadima (IL)

( * ) Notice: Subject to any disclaimer, the term of this patent is extended or adjusted under 35 U.S.C. 154(b) by 95 days.

(21) Appl. No.: 14/567,439

(22) Filed: Dec. 11, 2014

(65) Prior Publication Data

US 2015/0157777 A1    Jun. 11, 2015

Related U.S. Application Data

(60) Provisional application No. 61/914,470, filed on Dec. 11, 2013.

(51) Int. Cl.
*A61M 25/01* (2006.01)
*A61M 25/00* (2006.01)
(Continued)

(52) U.S. Cl.
CPC ...... *A61M 25/0023* (2013.01); *A61M 1/1024* (2014.02); *A61M 1/125* (2014.02); *A61M 25/0041* (2013.01)

(58) Field of Classification Search
CPC .... A61M 1/10; A61M 25/00; A61M 25/0023; A61M 25/0041; A61M 1/125;
(Continued)

(56) References Cited

U.S. PATENT DOCUMENTS 4,919,647 A    4/1990 Nash
4,954,055 A    9/1990 Raible et al.
(Continued)

FOREIGN PATENT DOCUMENTS

AU    2013205145 A1    5/2013
WO    90/13321    11/1990
(Continued)

OTHER PUBLICATIONS

An Office Action dated Feb. 22, 2016, which issued during the prosecution of U.S. Appl. No. 14/405,144.
(Continued)

*Primary Examiner* — Nathan R Price
*Assistant Examiner* — John Doubrava
(74) *Attorney, Agent, or Firm* — Sughrue Mion, PLLC

(57) ABSTRACT

Apparatus and methods are described including inserting a catheter into a subject's body via a vein of the subject's groin. The catheter is advanced distally such that a distal end of the catheter is disposed inside the subject's renal vein. Respective stabilizing portions of the catheter stabilize the catheter by being in contact with inner walls of, respectively, an iliac vein of the subject, and a vena cava of the subject. Subsequently, a medical device is deployed inside the renal vein by retracting the distal end of the catheter, such that the distal end of the catheter is in a retracted state, in which the respective stabilizing portions of the catheter still stabilize the catheter by being in contact with the inner walls of, respectively, the subject's iliac vein and the subject's vena cava. Other applications are also described.

7 Claims, 9 Drawing Sheets

(51) Int. Cl.
*A61M 1/10* (2006.01)
*A61M 1/12* (2006.01)

(58) Field of Classification Search
CPC .. A61B 2018/0404; A61B 2018/00511; A61N 1/36114; A61N 1/36117
See application file for complete search history.

(56) References Cited

U.S. PATENT DOCUMENTS

| | | | |
|---|---|---|---|
| 5,613,935 | A | 3/1997 | Jarvik |
| 5,713,730 | A | 2/1998 | Nose et al. |
| 5,749,855 | A | 5/1998 | Reitan |
| 5,772,693 | A | 6/1998 | Brownlee |
| 5,876,385 | A | 3/1999 | Ikari et al. |
| 5,964,694 | A | 10/1999 | Siess et al. |
| 6,086,527 | A | 7/2000 | Talpade |
| 6,135,729 | A | 10/2000 | Aber |
| 6,247,892 | B1 | 6/2001 | Kazatchkov et al. |
| 6,482,228 | B1 | 11/2002 | Norred |
| 6,533,716 | B1 | 3/2003 | Schmitz-Rode et al. |
| 6,592,567 | B1 * | 7/2003 | Levin .............. A61M 25/0069 604/101.01 |
| 6,884,210 | B2 | 4/2005 | Nose et al. |
| 7,004,925 | B2 | 2/2006 | Navia et al. |
| 7,159,593 | B2 | 1/2007 | McCarthy et al. |
| 7,335,192 | B2 | 2/2008 | Keren et al. |
| 7,341,570 | B2 | 3/2008 | Keren et al. |
| 7,485,104 | B2 | 2/2009 | Kieval |
| 7,717,952 | B2 | 5/2010 | Case et al. |
| 7,744,642 | B2 | 6/2010 | Rittgers |
| 7,762,941 | B2 | 7/2010 | Jarvik |
| 7,766,892 | B2 | 8/2010 | Keren et al. |
| 7,766,961 | B2 | 8/2010 | Patel et al. |
| 7,780,628 | B1 | 8/2010 | Keren et al. |
| 7,811,221 | B2 | 10/2010 | Gross |
| 7,841,976 | B2 | 11/2010 | McBride et al. |
| 7,914,503 | B2 | 3/2011 | Goodson et al. |
| 8,012,121 | B2 | 9/2011 | Goodson et al. |
| 8,221,492 | B2 | 7/2012 | Case et al. |
| 8,235,933 | B2 | 8/2012 | Keren et al. |
| 8,277,470 | B2 | 10/2012 | Demarais et al. |
| 8,376,707 | B2 | 2/2013 | McBride et al. |
| 8,449,443 | B2 | 5/2013 | Rodefeld et al. |
| 8,512,262 | B2 | 8/2013 | Gertner |
| 8,538,535 | B2 | 9/2013 | Gross et al. |
| 8,579,858 | B2 | 11/2013 | Reitan et al. |
| 8,617,239 | B2 | 12/2013 | Reitan |
| 8,777,832 | B1 | 7/2014 | Wang et al. |
| 9,138,518 | B2 | 9/2015 | Campbell et al. |
| 9,358,329 | B2 | 6/2016 | Fitzgerald et al. |
| 2003/0055486 | A1 | 3/2003 | Adams et al. |
| 2004/0064090 | A1 | 4/2004 | Keren et al. |
| 2004/0116769 | A1 | 6/2004 | Jassawalla et al. |
| 2004/0167415 | A1 | 8/2004 | Gelfand et al. |
| 2004/0210236 | A1 | 10/2004 | Allers et al. |
| 2004/0260389 | A1 | 12/2004 | Case et al. |
| 2005/0033406 | A1 | 2/2005 | Barnhart et al. |
| 2005/0049692 | A1 | 3/2005 | Numamoto et al. |
| 2005/0079274 | A1 | 4/2005 | Palasis et al. |
| 2006/0106449 | A1 | 5/2006 | Muvhar |
| 2007/0100435 | A1 | 5/2007 | Case et al. |
| 2007/0162103 | A1 | 7/2007 | Case et al. |
| 2007/0208291 | A1 | 9/2007 | Patel |
| 2007/0260327 | A1 | 11/2007 | Case et al. |
| 2008/0103591 | A1 | 5/2008 | Siess |
| 2008/0132748 | A1 | 6/2008 | Shifflette |
| 2008/0154236 | A1 | 6/2008 | Elkins et al. |
| 2008/0183280 | A1 | 7/2008 | Agnew et al. |
| 2009/0024195 | A1 | 1/2009 | Rezai et al. |
| 2009/0062597 | A1 | 3/2009 | Shifflette |
| 2009/0093796 | A1 | 4/2009 | Pfeffer et al. |
| 2009/0264991 | A1 | 10/2009 | Paul, Jr. |
| 2009/0287299 | A1 | 11/2009 | Tabor et al. |
| 2009/0318857 | A1 | 12/2009 | Goodson et al. |
| 2010/0130810 | A1 | 5/2010 | Mohl |
| 2011/0004046 | A1 | 1/2011 | Campbell et al. |
| 2011/0106244 | A1 | 5/2011 | Ferrari et al. |
| 2011/0152999 | A1 | 6/2011 | Hastings et al. |
| 2011/0190874 | A1 | 8/2011 | Celermajer et al. |
| 2011/0213408 | A1 | 9/2011 | Gross et al. |
| 2011/0230949 | A1 | 9/2011 | Haverkost et al. |
| 2011/0264075 | A1 | 10/2011 | Leung et al. |
| 2011/0282128 | A1 | 11/2011 | Reitan et al. |
| 2011/0301662 | A1 | 12/2011 | Bar-Yoseph et al. |
| 2012/0022579 | A1 | 1/2012 | Fulton |
| 2012/0059460 | A1 * | 3/2012 | Reitan ................. A61M 1/101 623/3.12 |
| 2012/0089047 | A1 * | 4/2012 | Ryba ................... A61B 18/02 600/554 |
| 2012/0116382 | A1 | 5/2012 | Ku et al. |
| 2012/0130469 | A1 | 5/2012 | Cragg et al. |
| 2012/0224970 | A1 | 9/2012 | Schumacher et al. |
| 2013/0053623 | A1 | 2/2013 | Evans et al. |
| 2013/0053732 | A1 | 2/2013 | Heuser |
| 2014/0025041 | A1 * | 1/2014 | Fukuoka ........... A61M 25/0041 604/523 |
| 2014/0128659 | A1 | 5/2014 | Heuring et al. |
| 2014/0275722 | A1 | 9/2014 | Zimmermann et al. |
| 2015/0176582 | A1 | 6/2015 | Liebing |
| 2015/0343136 | A1 | 12/2015 | Nitzan et al. |
| 2015/0343186 | A1 | 12/2015 | Nitzan et al. |
| 2016/0053768 | A1 | 2/2016 | Schumacher et al. |
| 2016/0279310 | A1 | 9/2016 | Scheckel et al. |

FOREIGN PATENT DOCUMENTS

| | | |
|---|---|---|
| WO | 94/01148 A1 | 1/1994 |
| WO | 99/34847 | 7/1999 |
| WO | 02/38085 A1 | 5/2002 |
| WO | 03/006096 | 1/2003 |
| WO | 03/103745 | 12/2003 |
| WO | 2004/073796 | 9/2004 |
| WO | 2005/020848 A2 | 3/2005 |
| WO | 2008055301 A1 | 5/2008 |
| WO | 2009/010963 | 1/2009 |
| WO | 2009/129481 A1 | 10/2009 |
| WO | 2011/035926 A1 | 3/2011 |
| WO | 2011/076441 A1 | 6/2011 |
| WO | 2012/007141 A1 | 1/2012 |
| WO | 2013/032849 | 3/2013 |
| WO | 2013/148697 A1 | 10/2013 |
| WO | 2013/183060 | 12/2013 |
| WO | 2014/141284 | 9/2014 |
| WO | 2015/063277 A2 | 5/2015 |

OTHER PUBLICATIONS

An International Search Report and a Written Opinion both dated Jan. 27, 2016, which issued during the prosecution of Applicant's PCT/IL2015/050532.

European Search Report dated Feb. 5, 2016, which issued during the prosecution of Applicant's European App No. 13800935.

McAlister, et al. Renal Insufficiency and Heart Failure: Prognostic and Therapeutic Implications Circulation 2004;109;1004-1009.

Forman, et al. Incidence, Predictors at Admission, and Impact of Worsening Renal Function Among Patients Hospitalized With Heart Failure. (J Am Coll Cardiol 2004;43:61-7).

Hillege, et al. Renal function as a predictor of outcome in a broad spectrum of patients with heart failure. Circulation 2006; 13:671-678.

Heywood et al. High prevalence of renal dysfunction and its impact on outcome in 118,465 patients hospitalized with acute decompensated heart failure: a report from the ADHERE database. J Cardiac Fail 2007;13:422-430.

Hillege, et al. Renal function, neurohormonal activation, and survival in patients with chronic heart failure. Circulation 2000;102;203-2106.

Yancy, et al. Clinical presentation, management, and in-hospital outcomes of patients admitted with acute decompensated heart failure with preserved systolic function: A report from the Acute

(56) References Cited

OTHER PUBLICATIONS

Decompensated Heart Failure National Registry (ADHERE) databaseJournal of the American College of Cardiology 2006;47(1):76-84.
Mullens, et al. Importance of venous congestion for worsening of renal function in advanced decompensated heart failure.J Am Coll Cardiol 2009;53:589-96.
Damman et al. Increased central venous pressure is associated with impaired Renal function and mortality in a broad spectrum of patients with cardiovascular disease. J Am Coll Cardiol 2009;53:582-8.
Uthoff et al. Central venous pressure at emergency room presentation predicts cardiac rehospitalization in patients with decompensated heart failure. European Journal of Heart Failure (2010) 12, 469-476.
Winton. The control of glomerular pressure by vascular changes within the mammalian kidney, demonstrated by the actions of adrenaline. J Physiol 1931,73:151-162.
Firth et al: Raised venous pressure: a direct cause of sodium retention in oedema? Lancet 1988;1:1033-1035.
Burnett and Knox. Renal interstitial pressure and sodium excretion during renal vein constriction. Am J Physiol 1980;F279-F282c.
Doty, et al. Effect of increased renal venous pressure on renal function. The Journal of Trauma: Injury, Infection, and Critical Care, Issue: vol. 47(6), Dec. 1999, p. 1000.
Felker, et al. Anemia as a risk factor and therapeutic target in heart failure J Am Coll Cardiol 2004;44:959-966.
Tang, Katz. Anemia in chronic heart failure: prevalence, etiology, clinical correlates, and treatment options Circulation 2006;113:2454-246116.
Mullens, et al. Elevated Intra-Abdominal Pressure in Acute Decompensated Heart Failure. A Potential Contributor to Worsening Renal Function?
Mullens, et al. Prompt Reduction in Intra-Abdominal Pressure Following Large-Volume Mechanical Fluid Removal Improves Renal Insufficiency in Refractory Decompensated Heart Failure. Journal of Cardiac Failure vol. 14 No. 6 2008.
Notarius, Magder. Central venous pressure during exercise: role of muscle pump, Canadian Journal of Physiology and Pharmacology, 1996, 74(6): 647-651.
Wood. The mechanism of the increased venous pressure with exercise in congestive heart failure. J clin invest 1962;41(11):220-2024.
Lauten, et al. Heterotopic transcatheter tricuspid valve implantation: first-in-man application of a novel approach to tricuspid regurgitation. Eur Heart J (2011) 32 (10): 1207-1213.
Ben Coxworth; Artificial vein valve could replace drugs for treating common circulatory problem. Published on Gizmag website (http://www.gizmag.com/artificial-venous-valve-cvi/21785/), Mar. 9, 2012.
Gomes et al.; Heterologous valve implantation in the infra-renal vena cava for treatment of the iliac venous valve regurgitation disease: experimental study; Rev Bras Cir Cardiovasc 2002; 17(4): 367-369.
Park et al.; Nutcracker syndrome: Intravascular stenting approach; Nephroi Dial Transplant (2000) 15:99-101.
Schmitz-Rode et al.; An Expandable Percutaneous Catheter Pump for Left Ventricular Support; Journal of the American College of Cardiology vol. 45, No. 11, 2005.
Damman et al,; Decreased cardiac output, venous congestion and the association with renal impairment in patients with cardiac dysfunction, European Journal of Heart Failure 9 (2007) 872-878.
F. R. Winton, The influence of venous pressure on the isolated mammalian kidney; J Physiol. Jun. 6, 1931; 72(1): 49-61.
Detlef Wencker, Acute Cardio-renal Syndrome: Progression from Congestive Heart Failure to Congestive Kidney Failure; Current Heart Failure Reports 2007, 4:134-138.
S. J. G. Semple et al., Effect of Increased Renal Venous Pressure on Circulatory "Autoregulation" of Isolated Dog Kidneys; Circ Res. 1959;7:643-648.
F. J. Haddy, Effect of Elevation of Intraluminal Pressure on Renal Vascular Resistance, Circ Res. 1956;4:659-663.
Y. Ikari, The Physics of Guiding Catheter; The IKARI Guiding Catheter in TRI; available at http://www.docstoc.com/docs/148136553/The-IKARI-catheter---a-novel-guide-for-TRI--, uploaded on Mar. 8, 2013.
An International Search Report dated Nov. 22, 2013, which issued during the prosecution of Applicant's PCT/IL2013/050495.
An International Search Report dated Sep. 11, 2014, which issued during the prosecution of Applicant's PCT/IL2014/050289.
U.S. Appl. No. 61/914,470, filed Dec. 11, 2013.
An Office Action dated Oct. 3, 2016, which issued during the prosecution of U.S. Appl. No. 14/931,363.
European Search Report dated Sep. 28, 2016, which issued during the prosecution of Applicant's European App No. 14762232.8.
Timms, Daniel. "A review of clinical ventricular assist devices." Medical engineering & physics 33.9 (2011): 1041-1047.
Wu, Huachun, Ziyan Wang, and Xujun Lv. "Design and simulation of axial flow maglev blood pump." International Journal of Information Engineering and Electronic Business 3.2 (2011): 42.
Thunberg, Christopher A., et al. "Ventricular assist devices today and tomorrow." Journal of cardiothoracic and vascular anesthesia 24.4 (2010): 656-680.
Throckmorton, Amy L., and Ravi A. Kishore. "Design of a protective cage for an intravascular axial flow blood pump to mechanically assist the failing Fontan." Artificial organs 33.8 (2009): 611-621.
Song, Xinwei, et al. "Axial flow blood pumps." ASAIO journal 49 (2003): 355-364.
Reul, Helmut M., and Mustafa Akdis. "Blood pumps for circulatory support." Perfusion-Sevenoaks-15.4 (2000): 295-312.
Alba, Ana C., and Diego H. Delgado. "The future is here: ventricular assist devices for the failing heart." Expert review of cardiovascular therapy 7.9 (2009): 1067-1077.
Koochaki, Mojtaba, and Hanieh Niroomand-Oscuii. "A new design and computational fluid dynamics study of an implantable axial blood pump." Australasian Physical & Engineering Sciences in Medicine 36.4 (2013): 417-422.
Kang, Can, Qifeng Huang, and Yunxiao Li. "Fluid dynamics aspects of miniaturized axial-flow blood pump." Bio-medical materials and engineering 24.1 (2014): 723-729.
Kafagy, Dhyaa H., et al. "Design of axial blood pumps for patients with dysfunctional fontan physiology: computational studies and performance testing." Artificial organs 39.1 (2015): 34-42.
Hsu, Po-Lin, et al. "Review of recent patents on foldable ventricular assist devices." Recent Patents on Biomedical Engineering 5.3 (2012): 208-222.
Fraser, Katharine H., et al. "The use of computational fluid dynamics in the development of ventricular assist devices." Medical engineering & physics 33.3 (2011): 263-280.
Agarwal, Shvetank, and Kane M. High. "Newer-generation ventricular assist devices." Best Practice & Research Clinical Anaesthesiology 26.2 (2012): 117-130.
An Office Action together with the English translation dated Mar. 22, 2017, which issued during the prosecution of Chinese Patent Application No. 201380037335.4.
An Office Action dated Feb. 15, 2017, which issued during the prosecution of U.S. Appl. No. 14/931,363.

\* cited by examiner

CURVED CATHETER

CROSS-REFERENCES TO RELATED APPLICATIONS

The present application claims the benefit of U.S. Provisional Patent Application 61/914,470 to Tuval, filed Dec. 11, 2013, entitled "Curved catheter."

The present application is related to:

U.S. patent application Ser. No. 14/405,144 to Tuval (published as US 2015-0164662), which is the US National Phase of International Patent Application PCT/IL2013/050495 to Tuval (published as WO 13/183060), filed Jun. 6, 2013, entitled "Prosthetic renal valve," which claims priority from U.S. Provisional Patent Application 61/656,244 to Tuval, filed Jun. 6, 2012, entitled "Prosthetic renal valve;" and International Patent Application PCT/IL2014/050289 to Schwammenthal (published as WO 14/141284), filed Mar. 13, 2014, entitled "Renal pump," which claims priority from (a) U.S. Provisional Patent Application 61/779,803 to Schwammenthal, filed Mar. 13, 2013, entitled "Renal pump," and (b) U.S. Provisional Patent Application 61/914,475 to Schwammenthal, filed Dec. 11, 2013, entitled "Renal pump."

All of the above-listed applications are incorporated herein by reference.

FIELD OF EMBODIMENTS OF THE INVENTION

Some applications of the present invention generally relate to medical apparatus. Specifically, some applications of the present invention relate to apparatus and methods associated with placing a medical device in one or more of a subject's renal vessels.

BACKGROUND

Catheters are medical tools that are used for cardiovascular, urological, gastrointestinal, neurovascular, and ophthalmic applications. Catheters may be inserted blood vessels, such as to provide access to the blood vessel to medical devices or tools. Catheters are typically flexible tubes that are inserted into a patient's body via an access port and advanced, over a guidewire, to a desired location inside the subject's body.

SUMMARY OF EMBODIMENTS

In accordance with some applications of the present invention, a catheter is placed into a renal vessel of a subject by being inserted into the subject's vasculature via a vessel of the subject's groin. The catheter defines a continuous tube that defines a lumen therethrough, and a medical device is inserted into the subject's body via the catheter lumen. The continuous tube defined by the catheter typically defines at least a first portion, a second portion, a third portion, a fourth portion, and a fifth portion thereof, each of the portions of the catheter typically defining a shape having given characteristics.

The catheter is typically shaped such that both (a) when the catheter is placed into a renal vessel that is ipsilateral with respect to the vessel of the groin via which the catheter is inserted, and (b) when the catheter is placed into a renal vessel that is contralateral with respect to the vessel of the groin via which the catheter is inserted, the catheter is stabilized by portions of the catheter contacting inner walls of the blood vessels of the subject at at least two points. Typically, one of the portions of the catheter stabilizes the catheter by contacting an inner wall of an iliac vessel of the subject, and another one of the portions of the catheter stabilizes the catheter by contacting an inner wall of the vena cava, or the aorta of the subject. Further typically, the catheter is stabilized by portions of the catheter contacting inner walls of the blood vessels of the subject at the at least two points (a) before the catheter is retracted such as to release the device from the distal end of the catheter, and (b) subsequent to the catheter having been retracted, such as to release the device from the distal end of the catheter.

There is therefore provided, in accordance with some applications of the present invention, apparatus including:

a medical device that is configured to be inserted into a body of a subject; and a catheter that defines a continuous tube that defines a lumen therethrough, the medical device being configured to be inserted into the subject's body via the catheter, the continuous tube including at least first, second, third, fourth, and fifth portions thereof, the first portion being disposed at a first end of the catheter and being shaped, when the catheter is in a non-constrained configuration, to define a cylindrical portion of the tube that defines a generally straight central longitudinal axis;

the second portion being disposed adjacent to the first portion and being shaped, when the catheter is in the non-constrained configuration, to define a curved cylindrical portion of the tube, a curvature of the second portion being such that a central longitudinal axis of the second portion defines a curve that is concave in a given direction, and that curves outwardly away from the central longitudinal axis of the first portion;

the third portion being disposed between the second and the fourth portions and being shaped, when the catheter is in the non-constrained configuration, to define a curved cylindrical portion of the tube, a curvature of the third portion being such that a central longitudinal axis of the third portion defines a curve that is convex in the given direction, and that curves inwardly toward the central longitudinal axis of the first portion, such that the central longitudinal axis of the third portion meets the central longitudinal axis of the first portion, the fourth portion being disposed between the third and the fifth portions of the tube, and being shaped, when the catheter is in the non-constrained configuration, to define a curved cylindrical tube, a curvature of the fourth portion being such that a central longitudinal axis of the fourth portion defines a curve that is concave in the given direction, and that curves away from the central longitudinal axis of the first portion, the fifth portion being disposed at a second end of the catheter the fifth portion being shaped, when the catheter is in the non-constrained configuration, to define a curved cylindrical tube, a curvature of the fifth portion being such that a central longitudinal axis of the fifth portion defines a curve that is concave in the given direction, and that curves inwardly toward the central longitudinal axis of the first portion.

For some applications, the continuous tube defined by the catheter further includes a sixth portion disposed between the second and third portions of the tube, the sixth portion of the tube defining a cylindrical portion of the tube that defines a generally straight central longitudinal axis, when the catheter is in the non-constrained configuration.

For some applications, a flexibility of at least a distal tip of the fifth portion is greater than a flexibility of each of the first, second, third, and fourth portions.

For some applications, at least a tip of the fifth portion is atraumatic.

For some applications, when the catheter is in the non-constrained configuration, a radius of curvature of the second portion is greater than 50 mm. For some applications, when the catheter is in the non-constrained configuration, the radius of curvature of the second portion is less than 250 mm.

For some applications, when the catheter is in the non-constrained configuration, a radius of curvature of the third portion is greater than 20 mm. For some applications, when the catheter is in the non-constrained configuration, the radius of curvature of the third portion is less than 100 mm.

For some applications, when the catheter is in the non-constrained configuration, a radius of curvature of the fourth portion is greater than 10 mm. For some applications, when the catheter is in the non-constrained configuration, the radius of curvature of the fourth portion is less than 80 mm.

For some applications, when the catheter is in the non-constrained configuration, a radius of curvature of the fifth portion is greater than 50 mm. For some applications, when the catheter is in the non-constrained configuration, the radius of curvature of the fifth portion is less than 250 mm.

For some applications, when the catheter is in the non-constrained configuration, a ratio of a radius of curvature of the second portion to a radius of curvature of the third portion is greater than 1.5:1. For some applications, when the catheter is in the non-constrained configuration, the ratio of the radius of curvature of the second portion to the radius of curvature of the third portion is less than 4:1.

For some applications, when the catheter is in the non-constrained configuration, a length of the second portion of the tube, measured along the longitudinal axis of the second portion, is at least twice the length of the medical device. For some applications, the length of the second portion of the tube is at least 3 times the length of the medical device.

For some applications, a length of the third portion of the tube, measured along the longitudinal axis of the third portion, is at least twice the length of the medical device. For some applications, the length of the third portion of the tube is at least 3 times the length of the medical device.

For some applications, when the catheter is in the non-constrained configuration a length of the second portion, measured along the longitudinal axis of the second portion, is greater than 20 mm. For some applications, when the catheter is in the non-constrained configuration, the length of the second portion is less than 50 mm.

For some applications, when the catheter is in the non-constrained configuration, a length of the third portion, measured along the longitudinal axis of the third portion, is greater than 40 mm. For some applications, when the catheter is in the non-constrained configuration, the length of the third portion is less than 100 mm.

For some applications, when the catheter is in the non-constrained configuration, a length of the fourth portion, measured along the longitudinal axis of the fourth portion, is greater than 20 mm. For some applications, when the catheter is in the non-constrained configuration, the length of the fourth portion is less than 50 mm.

For some applications, when the catheter is in the non-constrained configuration, a length of the fifth portion, measured along the longitudinal axis of the fifth portion, is greater than 20 mm. For some applications, when the catheter is in the non-constrained configuration, the length of the fifth portion is less than 50 mm.

For some applications:
the catheter is configured to be:
inserted into the subject's body via a blood vessel of a groin of the subject, and
advanced distally such that the fifth portion of the catheter is inserted into a renal vessel that is contralateral to the blood vessel of the subject's groin; and
the medical device is configured to be deployed inside the contralateral renal vessel by the catheter being retracted proximally, subsequent to insertion of the fifth portion of the catheter into the contralateral renal vessel.

For some applications, when the fifth portion of the catheter is disposed inside the renal vessel and prior to deploying the medical device by the catheter being retracted proximally, the second portion is configured to stabilize the catheter by contacting an inner wall of an iliac vessel of the subject.

For some applications, when the fifth portion of the catheter is disposed inside the renal vessel, and prior to deploying the medical device by the catheter being retracted proximally, the third portion is configured to stabilize the catheter by contacting an inner wall of a vessel of the subject selected from the group consisting of: a vena cava of the subject, and an aorta of the subject.

For some applications, when the fifth portion of the catheter is disposed inside the renal vessel, and prior to deploying the medical device by the catheter being retracted proximally, the fourth portion is configured to stabilize the catheter by contacting an inner wall of the renal vessel.

For some applications, subsequent to deployment of the device in the contralateral renal vessel by the catheter having been retracted proximally, the second portion is configured to stabilize the catheter by contacting an inner wall of an iliac vessel of the subject.

For some applications, subsequent to deployment of the device in the contralateral renal vessel by the catheter having been retracted proximally, the third portion is configured to stabilize the catheter by contacting an inner wall of a vessel of the subject selected from the group consisting of: a vena cava of the subject, and an aorta of the subject.

For some applications, subsequent to deployment of the device in the contralateral renal vessel by the catheter having been retracted proximally, the fourth portion is configured to stabilize the catheter by contacting an inner wall of the renal vessel.

For some applications:
the catheter is configured to be:
inserted into the subject's body via a blood vessel of a groin of the subject, and
advanced distally such that the fifth portion of the catheter is inserted into a renal vessel that is ipsilateral to the blood vessel of the subject's groin; and
the medical device is configured to be deployed inside the contralateral renal vessel by the catheter being retracted proximally, subsequent to insertion of the fifth portion of the catheter into the ipsilateral renal vessel.

For some applications, when the fifth portion of the catheter is disposed inside the renal vessel, and prior to deploying the medical device by the catheter being retracted proximally, the second portion is configured to stabilize the catheter by contacting an inner wall of an iliac vessel of the subject.

For some applications, when the fifth portion of the catheter is disposed inside the renal vessel, and prior to deploying the medical device by the catheter being retracted proximally, the third portion is configured to stabilize the catheter by contacting an inner wall of a vessel of the subject selected from the group consisting of: a vena cava of the subject, and an aorta of the subject.

For some applications, when the fifth portion of the catheter is disposed inside the renal vessel, and prior to deploying the medical device by the catheter being retracted proximally, the fourth portion is configured to stabilize the catheter by contacting an inner wall of the renal vessel.

For some applications, subsequent to deployment of the device in the ipsilateral renal vessel by the catheter having been retracted proximally, the second portion is configured to stabilize the catheter by contacting an inner wall of an iliac vessel of the subject.

For some applications, subsequent to deployment of the device in the ipsilateral renal vessel by the catheter having been retracted proximally, the third portion is configured to stabilize the catheter by contacting an inner wall of a vessel of the subject selected from the group consisting of: a vena cava of the subject, and an aorta of the subject.

For some applications, subsequent to deployment of the device in the ipsilateral renal vessel by the catheter having been retracted proximally, the fourth portion is configured to stabilize the catheter by contacting an inner wall of the renal vessel.

For some applications, in the non-constrained configuration of the catheter, the catheter defines a span in a direction that is perpendicular to the longitudinal axis of the first portion that is greater than 20 mm.

For some applications, in the non-constrained configuration of the catheter, the catheter defines a span in the direction that is perpendicular to the longitudinal axis of the first portion that is greater than 40 mm.

For some applications, in the non-constrained configuration of the catheter, the catheter defines a span in the direction that is perpendicular to the longitudinal axis of the first portion that is less than 70 mm.

For some applications, in the non-constrained configuration of the catheter, the catheter defines a span in the direction that is perpendicular to the longitudinal axis of the first portion that is less than 60 mm.

For some applications, in the non-constrained configuration of the catheter, the catheter defines a length measured along the longitudinal axis of the first portion, from a location at which the longitudinal axis of the second portion begins to curve away from the longitudinal axis of the first portion until the longitudinal axis of the third portion meets the longitudinal axis of the first portion that is greater than 80 mm. For some applications, the length is greater than 100 mm. For some applications, the length is less than 250 mm. For some applications, the length is less than 150 mm.

For some applications, the medical device includes a radially-expandable impeller disposed inside a radially-expandable cage.

For some applications, a length of cage, measured along a longitudinal axis of the cage, when the cage is in a radially expanded configuration, is between 17 mm and 26 mm.

There is further provided, in accordance with some applications of the present invention, a method including:
inserting a catheter into a body of a subject via a vein of a groin of the subject, and
advancing the catheter distally such that:
a distal end of the catheter is disposed inside a renal vein of the subject, and
respective stabilizing portions of the catheter stabilize the catheter by being in contact with inner walls of, respectively, an iliac vein of the subject, and a vena cava of the subject; and
subsequently, deploying a medical device inside the renal vein by retracting the distal end of the catheter, such that the distal end of the catheter is in a retracted state, in which the respective stabilizing portions of the catheter still stabilize the catheter by being in contact with the inner walls of, respectively, the subject's iliac vein and the subject's vena cava.

For some applications, advancing the catheter distally includes advancing the catheter distally such that a further stabilizing portion of the catheter stabilizes the catheter by being in contact with an inner wall of the renal vein.

For some applications, retracting the distal end of the catheter includes retracting the distal end of the catheter, such that while the distal end of the catheter is in its retracted state, a further stabilizing portion of the catheter stabilizes the catheter by being in contact with an inner wall of the renal vein.

For some applications, advancing the catheter distally such that the distal end of the catheter is disposed inside the subject's renal vein includes advancing the catheter distally such that the distal end of the catheter is disposed inside a renal vein of the subject that is contralateral to the vein of the subject's groin via which the catheter is inserted.

For some applications, advancing the catheter distally such that the distal end of the catheter is disposed inside the subject's renal vein includes advancing the catheter distally such that the distal end of the catheter is disposed inside a renal vein of the subject that is ipsilateral to the vein of the subject's groin via which the catheter is inserted.

For some applications, the method further includes operating the medical device, inside the renal vein, while the catheter is disposed inside a body of the subject in its retracted state, such that the catheter supports the medical device during its operation.

For some applications, deploying the device includes deploying a radially-expandable impeller that is disposed inside a radially-expandable impeller cage, and operating the medical device includes rotating the impeller.

There is further provided, in accordance with some applications of the present invention, a method including:
inserting a catheter into a body of a subject via an artery of a groin of the subject, and
advancing the catheter distally such that:
a distal end of the catheter is disposed inside a renal artery of the subject, and
respective stabilizing portions of the catheter stabilize the catheter by being in contact with inner walls of, respectively, an iliac artery of the subject, and an aorta of the subject; and
subsequently, deploying a medical device inside the renal artery by retracting the distal end of the catheter, such that the distal end of the catheter is in a retracted state, in which the respective stabilizing portions of the catheter still stabilize the catheter by being in contact with the inner walls of, respectively, the subject's iliac artery and the subject's aorta.

For some applications, advancing the catheter distally includes advancing the catheter distally such that a further stabilizing portion of the catheter stabilizes the catheter by being in contact with an inner wall of the renal artery.

For some applications, retracting the distal end of the catheter includes retracting the distal end of the catheter, such that while the distal end of the catheter is in its retracted state, a further stabilizing portion of the catheter stabilizes the catheter by being in contact with an inner wall of the renal artery.

For some applications, advancing the catheter distally such that the distal end of the catheter is disposed inside the subject's renal artery includes advancing the catheter distally such that the distal end of the catheter is disposed inside a renal artery of the subject that is contralateral to the artery of the subject's groin via which the catheter is inserted.

For some applications, advancing the catheter distally such that the distal end of the catheter is disposed inside the subject's renal artery includes advancing the catheter distally such that the distal end of the catheter is disposed inside a renal artery of the subject that is ipsilateral to the artery of the subject's groin via which the catheter is inserted.

For some applications, the method further includes operating the medical device, inside the renal artery, while the catheter is disposed inside a body of the subject in its retracted state, such that the catheter supports the medical device during its operation.

For some applications, deploying the device includes deploying a radially-expandable impeller that is disposed inside a radially-expandable impeller cage, and operating the medical device includes rotating the impeller.

The present invention will be more fully understood from the following detailed description of embodiments thereof, taken together with the drawings, in which:

DETAILED DESCRIPTION OF EMBODIMENTS

Figure 1:
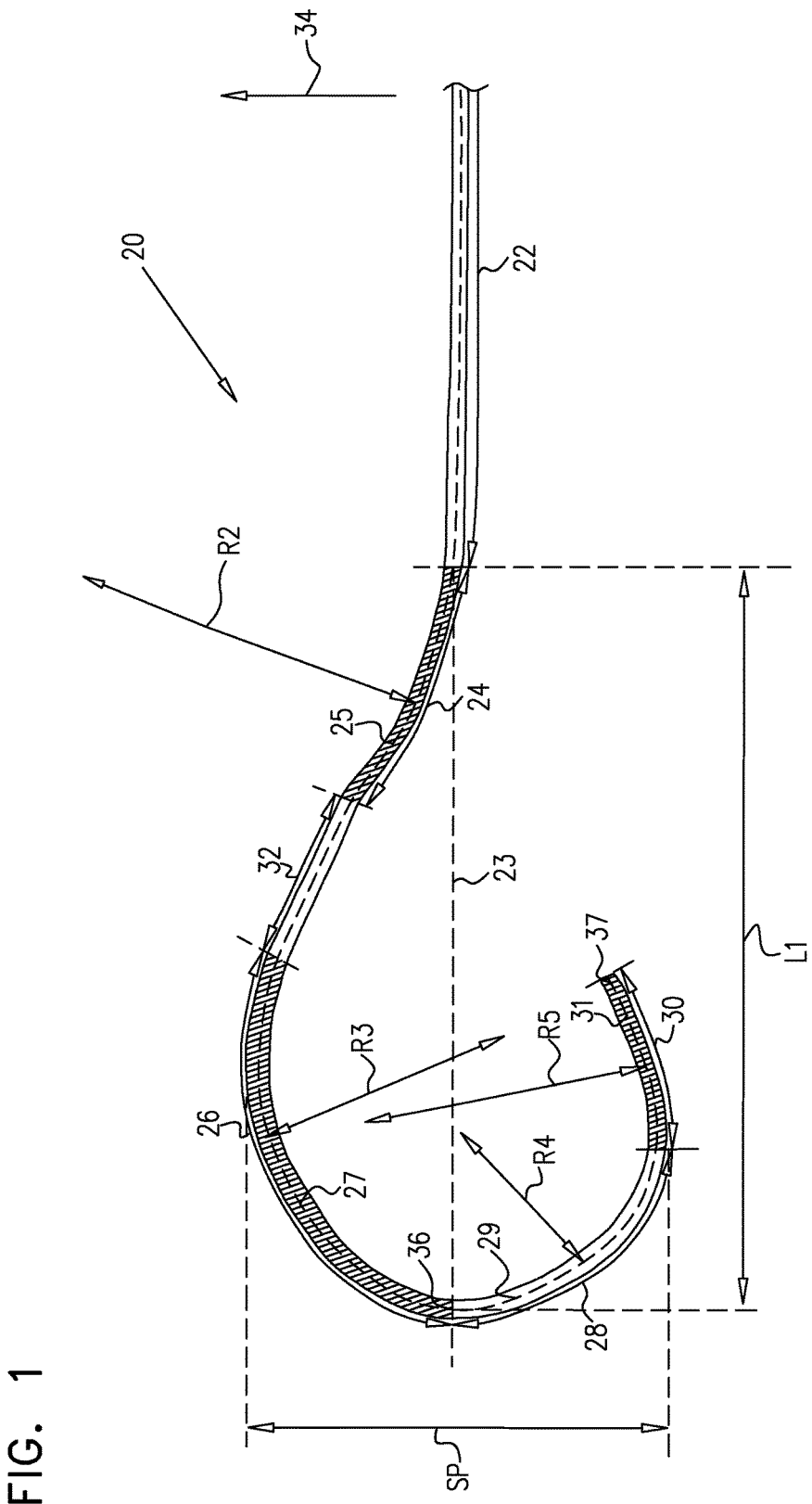
FIG. 1 is a schematic illustration of a catheter, in accordance with some applications of the present invention.

Reference is now made to FIG. 1, which is a schematic illustration of a catheter 20, in accordance with some applications of the present invention. Catheter 20 defines a continuous tube that defines a lumen therethrough. A medical device 50 (FIG. 2D) is typically inserted into the subject's body via the catheter lumen. The continuous tube defined by catheter 20 typically defines at least a first portion 22, a second portion 24, a third portion 26, a fourth portion 28, and a fifth portion 30 thereof. For some applications, the continuous tube additionally defines a sixth portion 32 having characteristics as described hereinbelow. Alternatively or additionally, the continuous tube defines one or more different additional portions.

Typically, in a non-constrained configuration of the catheter (i.e., in the absence of any force being applied to the catheter), each of the portions of the catheter defines a shape having characteristics as described hereinbelow. For some applications, the catheter is made from a polymer, a polymer that is reinforced with a braided or coiled metal or alloy, a metal, and/or an alloy (such as nitinol). The catheter is shape set (e.g., by shape setting the catheter in a mold, by steam shaping, and/or by mechanical shape setting), such that the shape of each of the portions has the described characteristics.

First portion 22 of catheter 20 is disposed at a first, proximal end of the catheter. When the catheter is in the non-constrained configuration, the first portion typically defines a cylindrical portion of the tube that defines a generally straight central longitudinal axis 23.

As used in the present application, including in the claims, a "central longitudinal axis" of a structure is the set of all centroids of cross-sectional sections of the structure along the structure. Thus the cross-sectional sections are locally perpendicular to the central longitudinal axis, which runs along the structure. (If the structure is circular in cross-section, the centroids correspond with the centers of the circular cross-sectional sections.)

Second portion 24 is typically disposed adjacent to the first portion. When the catheter is in the non-constrained configuration, the second portion is typically shaped to define a curved cylindrical portion of the tube. The curvature of the second portion is such that a central longitudinal axis 25 of the second portion defines a curve that is concave in a given direction, and that curves outwardly away from the central longitudinal axis of the first portion. For example, as shown in FIG. 1 the curve is concave in the direction in which arrow 34 is pointing.

For some applications, when the catheter is in the non-constrained configuration, a radius of curvature R2 of second portion 24 is greater than 50 mm, and/or less than 250 mm, e.g., 50 mm-250 mm. Typically, a length of the second portion of the tube (measured along central longitudinal axis 25 of the second portion) is at least twice the length (e.g., at least 3 times the length) of medical device 50 (FIG. 2D), which is configured to be placed inside the subject's body, via the catheter. For some applications, when the catheter is in the non-constrained configuration, the length of the second portion of the tube is greater than 20 mm, and/or less than 50 mm, e.g., 20 mm-50 mm.

Third portion 26 of catheter 20 is disposed between the second and the fourth portions. When the catheter is in the non-constrained configuration, the third portion is shaped to define a curved cylindrical portion of the tube. The curvature of the third portion is typically such that a central longitudinal axis 27 of the third portion defines a curve that is convex in the given direction (in the example shown, in the direction of arrow 34), and that curves inwardly toward the central longitudinal axis of the first portion. Further typically, the curvature of the third portion is such that the central longitudinal axis of the third portion meets central longitudinal axis 23 of the first portion. For example, as shown in FIG. 1, central longitudinal axis 27 of the third portion meets central longitudinal axis 23 of the first portion at point 36.

For some applications, when the catheter is in the non-constrained configuration, a radius of curvature R3 of third portion 26 is greater than 20 mm, and/or less than 100 mm, e.g., 20 mm-100 mm. For some applications, when the catheter is in the non-constrained configuration, a ratio of radius of curvature R2 of the second portion to radius of curvature R3 of the third portion is greater than 1.5:1, and/or less than 4:1, e.g., 1.5:1-4:1.

Typically, a length of the third portion of the tube (measured along central longitudinal axis 27 of the third portion) is at least twice the length (e.g., at least 3 times the length) of medical device 50 (FIG. 2D), which is configured to be placed inside the subject's body, via catheter 20. For some applications, when the catheter is in the non-constrained configuration, the length of the third portion of the tube is greater than 40 mm, and/or less than 100 mm, e.g., 40 mm-100 mm.

Fourth portion 28 is disposed between the third and the fifth portions of the tube. When the catheter is in the non-constrained configuration, the fourth portion typically defines a curved cylindrical tube. The curvature of the fourth portion is typically such that a central longitudinal axis 29 of the fourth portion defines a curve that is concave in the given direction (in the example shown, in the direction of arrow 34), and that curves away from central longitudinal axis 23 of first portion 22.

For some applications, when the catheter is in the non-constrained configuration, a radius of curvature R4 of fourth portion 28 is greater than 10 mm, and/or less than 80 mm, e.g., 10 mm-80 mm. For some applications, when the catheter is in the non-constrained configuration, a length of the fourth portion of the tube (measured along central longitudinal axis 29 of the fourth portion) is greater than 20 mm, and/or less than 50 mm, e.g., 20 mm-50 mm.

Fifth portion 30 is disposed at a second end of the catheter. When the catheter is in the non-constrained configuration, the fifth portion is typically shaped to define a curved cylindrical tube. The curvature of the fifth portion is typically such that a central longitudinal axis 31 of the fifth portion defines a curve that is concave in the given direction (in the example shown, in the direction of arrow 34), and that curves inwardly toward central longitudinal axis 23 of first portion 22. For some applications, at least a distal tip 37 of the fifth portion of the continuous tube defined by the catheter is greater than a flexibility of each of the first, second, third, and fourth portions.

For some applications, when the catheter is in the non-constrained configuration, a radius of curvature R5 of fifth portion 30 is greater than 50 mm, and/or less than 250 mm, e.g., 50 mm-250 mm. For some applications, when the catheter is in the non-constrained configuration, a length of the fifth portion of the tube (measured along central longitudinal axis 31 of the fifth portion) is greater than 20 mm, and/or less than 50 mm, e.g., 20 mm-50 mm.

As described hereinabove, for some applications, the tube defined by catheter 20 further defines a sixth portion 32, disposed between the second and third portions of the tube. For some applications, when the catheter is in the non-constrained configuration, the sixth portion of the tube defines a cylindrical portion of the tube that defines a generally straight central longitudinal axis. For some applications, a length of the sixth portion (measured along the central longitudinal axis of the sixth portion) is greater than 10 mm, and/or less than 100 mm, e.g., 10 mm-100 mm.

Typically, in the non-constrained configuration of the catheter (i.e., in the absence of any force being applied to the catheter), the catheter defines a span SP in a direction that is perpendicular to longitudinal axis 23 of first portion 22 that is greater than 20 mm (e.g., greater than 40 mm), and/or less than 70 mm (e.g., less than 60 mm), e.g., 20 mm-70 mm (e.g., 40 mm to 60 mm). Further typically, in the non-constrained configuration of the catheter (i.e., in the absence of any force being applied to the catheter), the catheter defines a length L1, measured along longitudinal axis 23 of first portion 22, from where the second catheter begins to curve until point 36 at which longitudinal axis 27 of third portion 26 meets longitudinal axis 23 of first portion 22 that is greater than 80 mm (e.g., greater than 100 mm), and/or less than 250 mm (e.g., less than 150 mm), e.g., 80 mm-250 mm (e.g., 100 mm to 150 mm). Typically, when the fifth portion of the catheter is placed inside a renal vessel of the subject, as described hereinbelow, length L1 corresponds to the distance from where the second portion of the catheter contacts the wall of an iliac vessel, until the renal vessel.

Figure 2A:
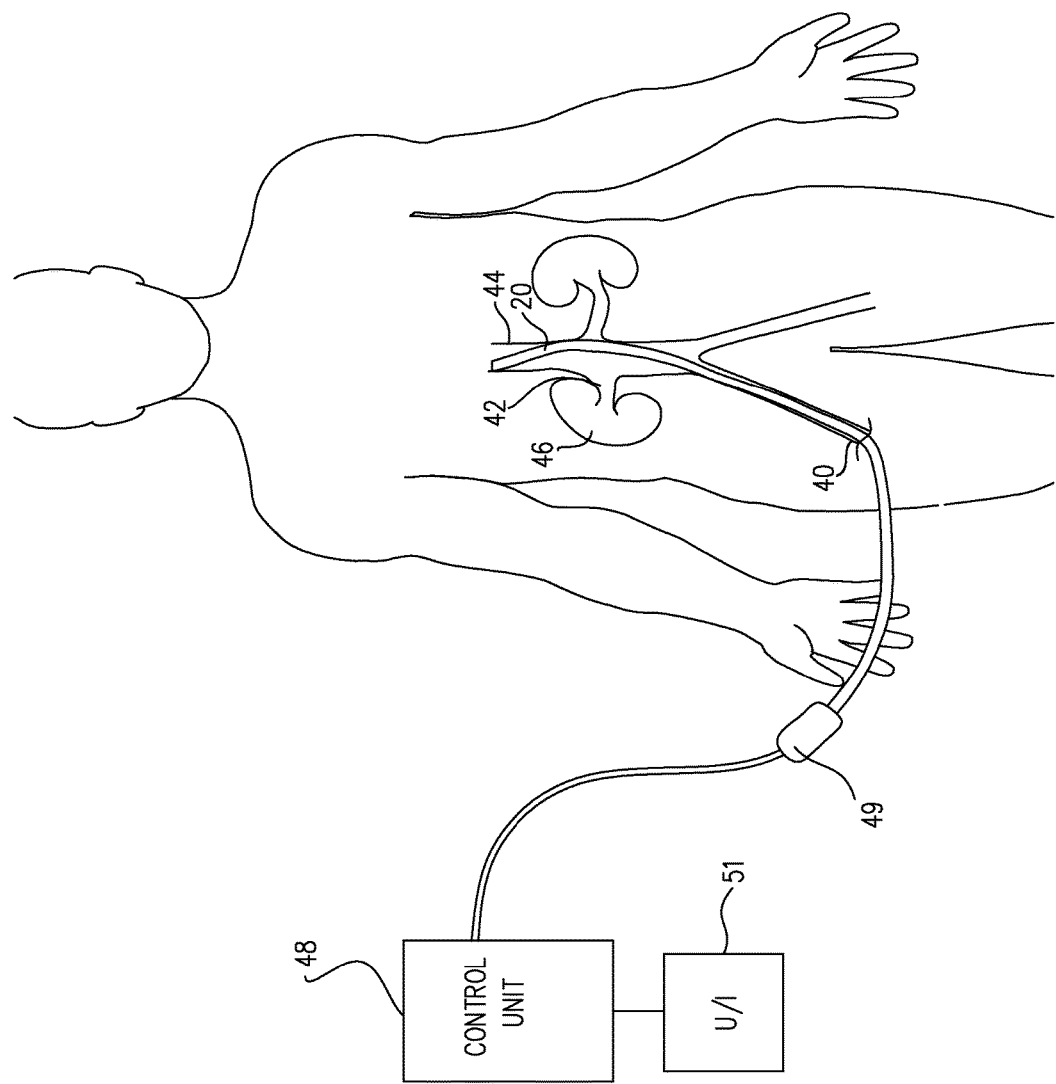
FIGS. 2A-B are schematic illustrations of the catheter being inserted via a vein of a subject's groin, a distal end of the catheter being placed into a renal vein of the subject that is ipsilateral to the vein of the groin, in accordance with some applications of the present invention.
Figure 2B:
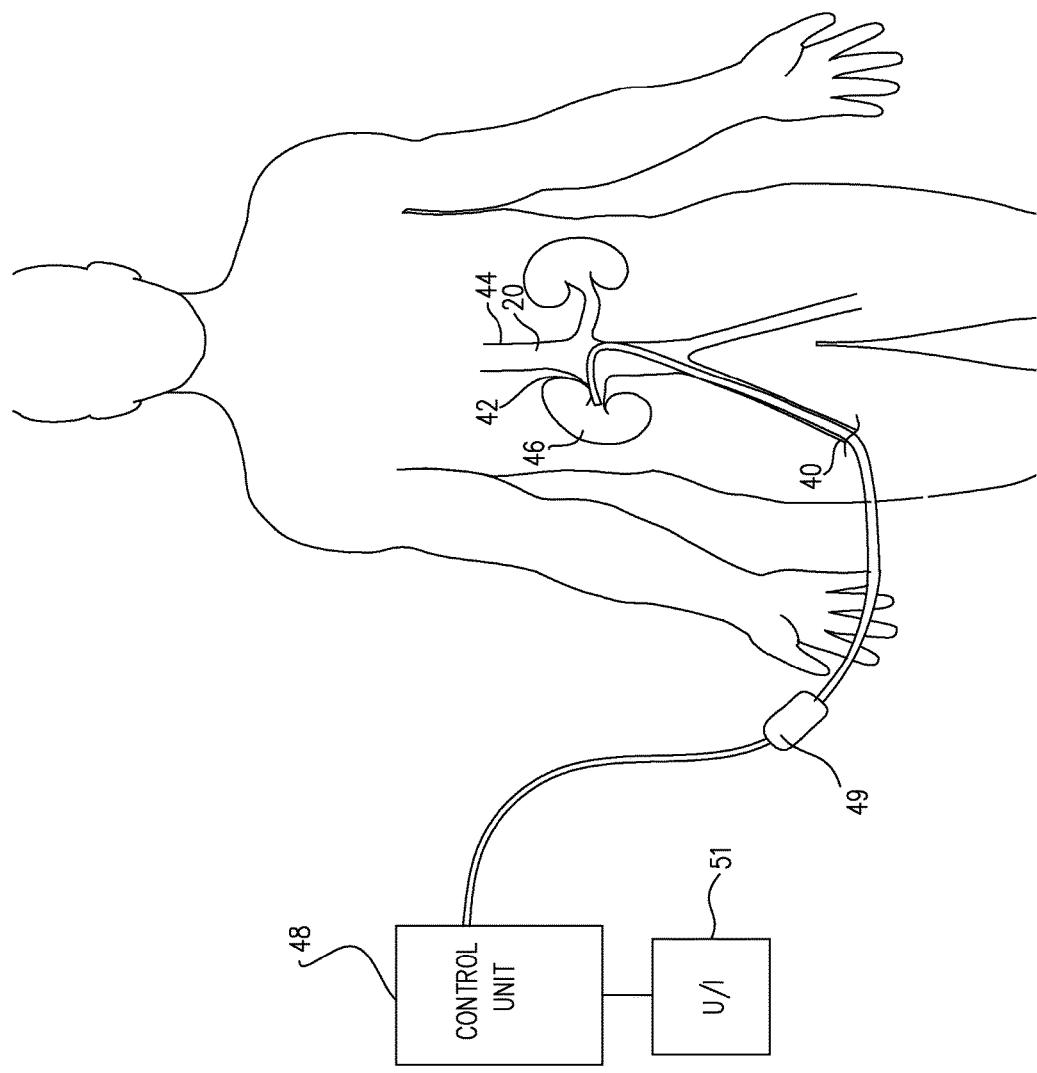

Reference is now made to FIGS. 2A-B, which are schematic illustrations of catheter 20 being inserted into the subject's vasculature via a vein of a subject's groin (right femoral vein 40, in the example shown). A distal end of the catheter is advanced into a renal vein of the subject that is ipsilateral to the vein of the groin (e.g., right renal vein 42, in the example shown), in accordance with some applications of the present invention. For some applications, in order to insert the distal end of the catheter into the renal vein, the distal end of the catheter is first placed into the subject's vena cava 44, downstream of (i.e., distal to) the renal vein. The catheter is inserted such that due to the curvature of the catheter, the distal tip of the catheter pushes against the inner wall of the vena cava on the ipsilateral side of the vena cava, as shown in FIG. 2A. The catheter is then retracted proximally, such that when the distal tip of the catheter passes the opening to the renal vein, the distal tip of the catheter enters the renal vein. When the distal tip has entered the renal vein, the catheter is then advanced, such that the distal tip of the catheter is disposed inside the renal vein in the vicinity of the subject's kidney 46, as shown in FIG. 2B.

As described hereinabove, typically, at least distal tip 37 of the fifth portion of the continuous tube defined by catheter 20 (i.e. the distal tip of the catheter) is greater than a flexibility of each of the first, second, third, and fourth portions of the catheter. For some applications, the distal tip of the fifth portion (i.e. the distal tip of the catheter) is thus configured to be atraumatic. For some applications, the tip being atraumatic reduces a likelihood of an injury being caused to the inner wall of the vena cava, during the insertion of the catheter, relative to if the distal tip of the catheter were not atraumatic. For some applications, the distal tip of the catheter is made of a more flexible material (e.g., a more flexible polymer) than that of the remainder of the catheter, and/or a reinforcing material (e.g., a braided or coiled metal or alloy) that reinforces the remainder of the catheter is not present in the distal tip of the catheter, or is made to be more flexible in the distal tip of the catheter.

For some applications, a control unit 48 disposed outside the subject's body is coupled to medical device 50 (FIG. 2D), and is configured to control the functioning of the medical device. For example, the medical device may be a pump, and the control unit may control the functioning of the pump, by rotating a portion of the pump via a motor 49.

Typically, the control unit includes any type of processor (such as a computer processor) configured to execute the actions described herein. Further typically, a user interacts with the control unit via a user interface 51, which typically includes any type of user interface configured to receive inputs from a user and/or to provide outputs to the user (including but not limited to keyboards, displays, pointing devices, etc.).

Figure 2D:
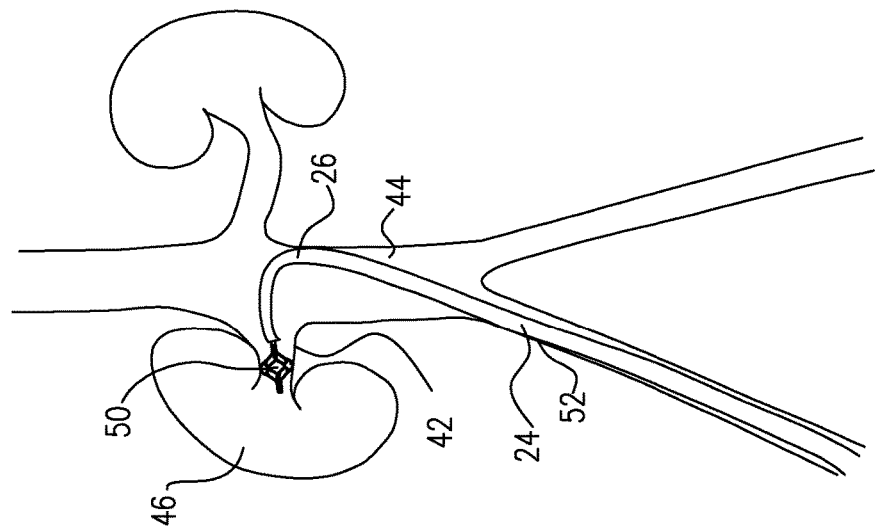
FIGS. 2C-D are schematic illustrations of portions of the catheter, respectively before and after a medical device has been deployed inside the ipsilateral renal vein, via the distal end of the catheter, in accordance with some applications of the present invention.
Figure 2C:
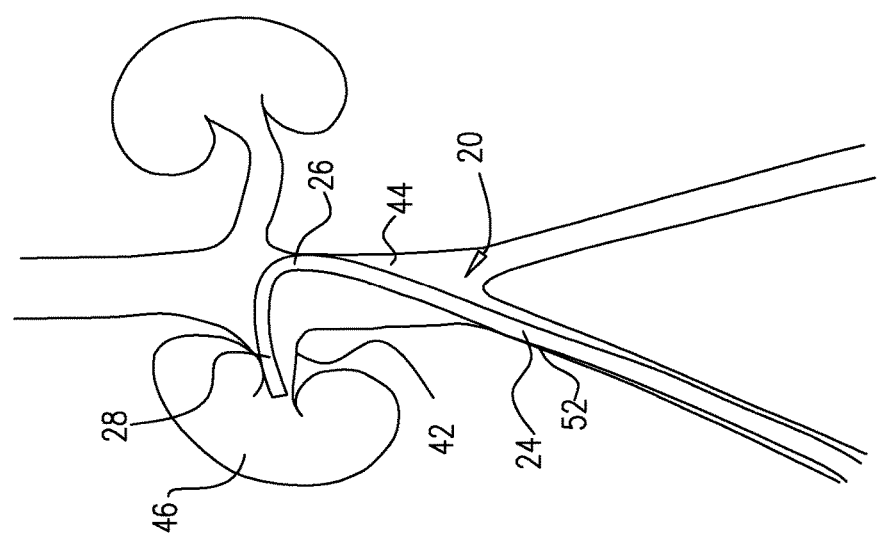

Reference is now made to FIGS. 2C-D, which are schematic illustrations of portions of catheter 20, respectively before and after a medical device 50 has been deployed inside renal vein 42, via the distal end of the catheter, in accordance with some applications of the present invention. Typically, medical device 50 is self expandable. For example, medical device 50 may be a self expandable valve, a self expandable stent, and/or a self-expandable pump. For some applications, medical device 50 is a blood pump that includes a radially-expandable impeller disposed inside a radially-expandable impeller cage, e.g., as described with reference to 12Ai-22Cii of WO 14/141284 to Schwammenthal, which is incorporated herein by reference. For such applications, control unit 48 typically controls the functioning of the pump, by rotating the impeller of the pump via motor 49. Typically, the medical device is deployed inside the renal vein by retracting the distal end of catheter 20, such that the medical device self expands, as shown in the transition from FIG. 2C to FIG. 2D.

Typically, during deployment of medical device 50 inside renal vein (i.e., during retraction of catheter 20 from the position shown in FIG. 2C to the position shown in FIG. 2D), second portion 24 of the catheter is configured to stabilize the catheter by contacting an inner wall of an iliac vein 52 of the subject. Further typically, subsequent to the deployment of the medical device inside the renal vein, second portion 24 of the catheter is configured to stabilize the catheter by contacting the inner wall of iliac vein 52, as shown in FIG. 2D. In this manner, second portion 24 acts as a stabilizing portion of the catheter. For some applications, the device is temporarily placed inside the subject's renal vein, in order to provide an acute treatment to the subject. The catheter remains in place inside the subject's vasculature during the treatment, and the second portion of the catheter provides stabilization to the catheter by contacting the inner wall of iliac vein 52, as shown in FIG. 2D. Subsequent to the treatment being terminated, device 50 is withdrawn from the subject's renal vein via the catheter.

As described hereinabove, the length of second portion 24 of the tube defined by catheter 20 is typically at least twice the length (e.g., at least 3 times the length) of medical device 50. Typically, the second portion is thus configured to contact the inner wall of iliac vein 52 both (a) before the catheter has been retracted such as to release the device from the distal end of the catheter (as shown in FIG. 2C), and (b) subsequent to the catheter having been retracted at least by the length of the device, such as to release the device from the distal end of the catheter (as shown in FIG. 2D).

As described hereinabove, for some applications, medical device 50 is a blood pump that includes a radially-expandable impeller disposed inside a radially-expandable impeller cage, e.g., as described with reference to 12Ai-22Cii of WO 14/141284 to Schwammenthal, which is incorporated herein by reference. For such applications, the length of the cage, measured along the longitudinal axis of the cage, and when the cage is in a radially expanded configuration, is typically greater than 17 mm, less than 26 mm, and/or between 17 and 26 mm. For some applications, the length of second portion 24 of the tube defined by catheter 20 is at least 30 mm (e.g., at least 50 mm), and/or less than 80 mm (e.g., less than 65 mm).

Typically, during deployment of medical device 50 inside renal vein (i.e., during retraction of catheter 20 from the position shown in FIG. 2C to the position shown in FIG. 2D), third portion 26 of the catheter is configured to stabilize the catheter by contacting an inner wall of the subject's vena cava 44. Further typically, subsequent to the deployment of the medical device inside the renal vein, third portion 26 of the catheter is configured to stabilize the catheter by contacting the inner wall of the vena cava, as shown in FIG. 2D. In this manner, third portion 26 acts as a stabilizing portion of the catheter. As described hereinabove, the length of the third portion of the tube defined by catheter 20 is typically at least twice the length (e.g., at least 3 times the length) of medical device 50. Typically, the third portion is thus configured to contact the inner wall of vena cava 44 both (a) before the catheter has been retracted such as to release the device from the distal end of the catheter (as shown in FIG. 2C), and (b) subsequent to the catheter having been retracted at least by the length of the device, such as to release the device from the distal end of the catheter (as shown in FIG. 2D).

As described hereinabove, for some applications, medical device 50 is a blood pump that includes a radially-expandable impeller disposed inside a radially-expandable impeller cage, e.g., as described with reference to 12Ai-22Cii of WO 14/141284 to Schwammenthal, which is incorporated herein by reference. For such applications, the length of the cage, measured along the longitudinal axis of the cage, is typically greater than 17 mm, less than 26 mm, and/or between 17 and 26 mm. For some applications, the length of third portion 26 of the tube defined by catheter 20 is at least 30 mm (e.g., at least 50 mm), and/or less than 80 mm (e.g., less than 65 mm).

For some applications, during at least a portion of the deployment of medical device 50 inside renal vein 42, fourth portion 28 of the catheter is configured to stabilize the catheter by contacting an inner wall of the subject's renal vein. For example, as shown in FIG. 2C, prior to the retraction of catheter 20 such as to deploy device 50, the fourth portion stabilizes the catheter by contacting the inner wall of the renal vein. In this manner, fourth portion 28 acts as a stabilizing portion of the catheter. For some applications, fourth portion 28 of the catheter is configured to stabilize the catheter by contacting an inner wall of the subject's renal vein even after the device has been deployed by the catheter having been retracted proximally. Alternatively, fourth portion 28 of the catheter is configured not contact the inner wall of the subject's renal vein after the device has been deployed by the catheter having been retracted proximally, as shown in FIG. 2D.

Figure 2E:
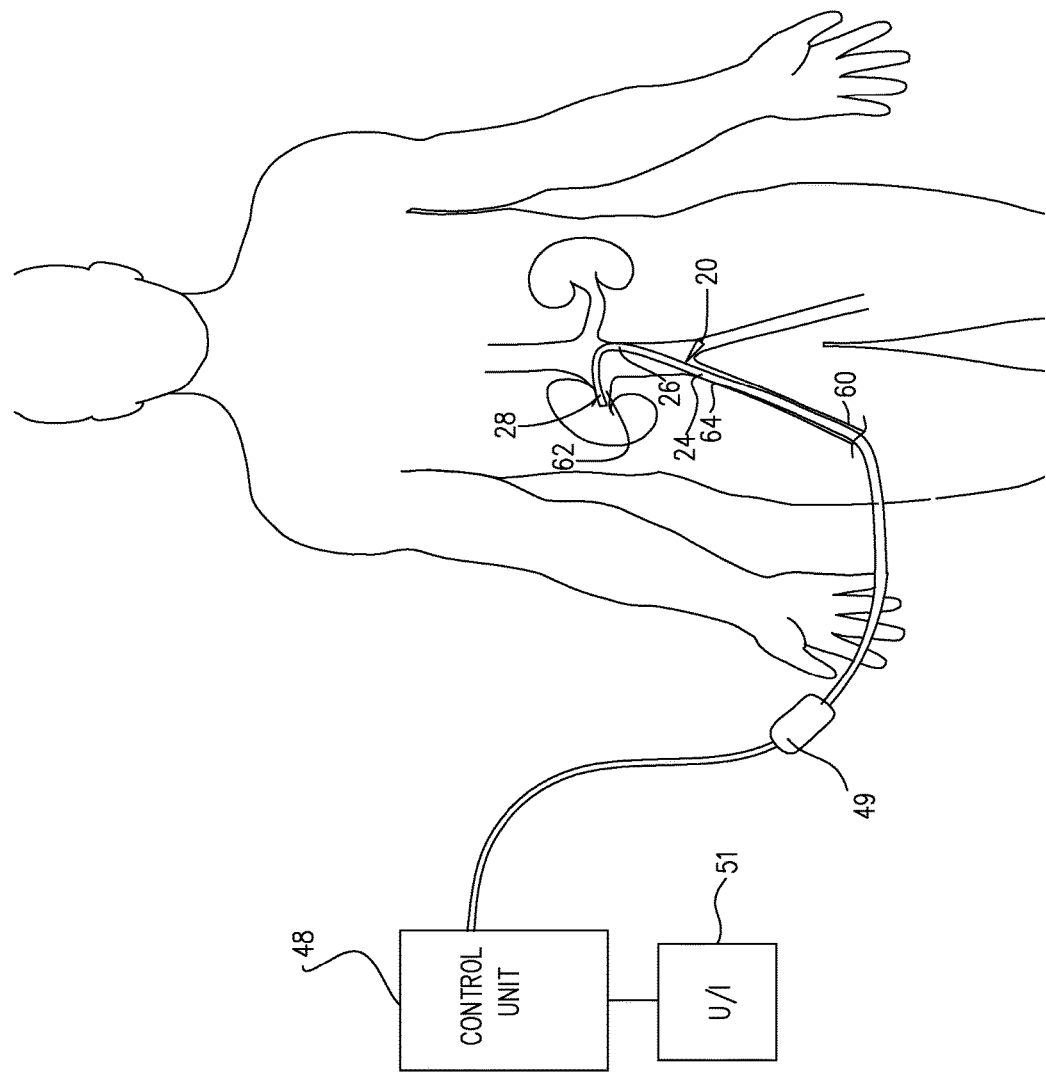
FIG. 2E is a schematic illustration of a catheter that has been inserted, via an artery of a subject's groin, such that a distal end of the catheter is placed into a renal artery of the subject that is ipsilateral to the artery of the groin, in accordance with some applications of the present invention.

Reference is now made to FIG. 2E, which is a schematic illustration of catheter 20, the catheter having been inserted into the subject's vasculature via an artery of a subject's groin (right femoral artery 60, in the example shown). A distal end of the catheter is advanced into a renal artery of the subject that is ipsilateral to the artery of the groin (e.g., right renal artery 62, in the example shown). For some applications, generally similar techniques to those described hereinabove with reference to FIGS. 2A-2D are performed on the arterial side of the subject's vasculature, mutatis mutandis. For some applications, when catheter 20 is used on the arterial side of the subject's vasculature, during at least a portion of the procedure (a) second portion 24 of the catheter stabilizes the catheter by contacting an inner wall of an iliac artery 64 of the subject, (b) third portion 26 of the catheter stabilizes the catheter by contacting an inner wall of an aorta 66 of the subject, and (c) fourth portion 28 of the catheter stabilizes the catheter by contacting an inner wall of renal artery 62. Typically, both before and after the catheter is retracted such as to release device 50 inside the renal artery, (a) second portion 24 of the catheter stabilizes the catheter by contacting the inner wall of iliac artery 64, and (b) third portion 26 of the catheter stabilizes the catheter by contacting the inner wall of aorta 66.

Figure 3A:
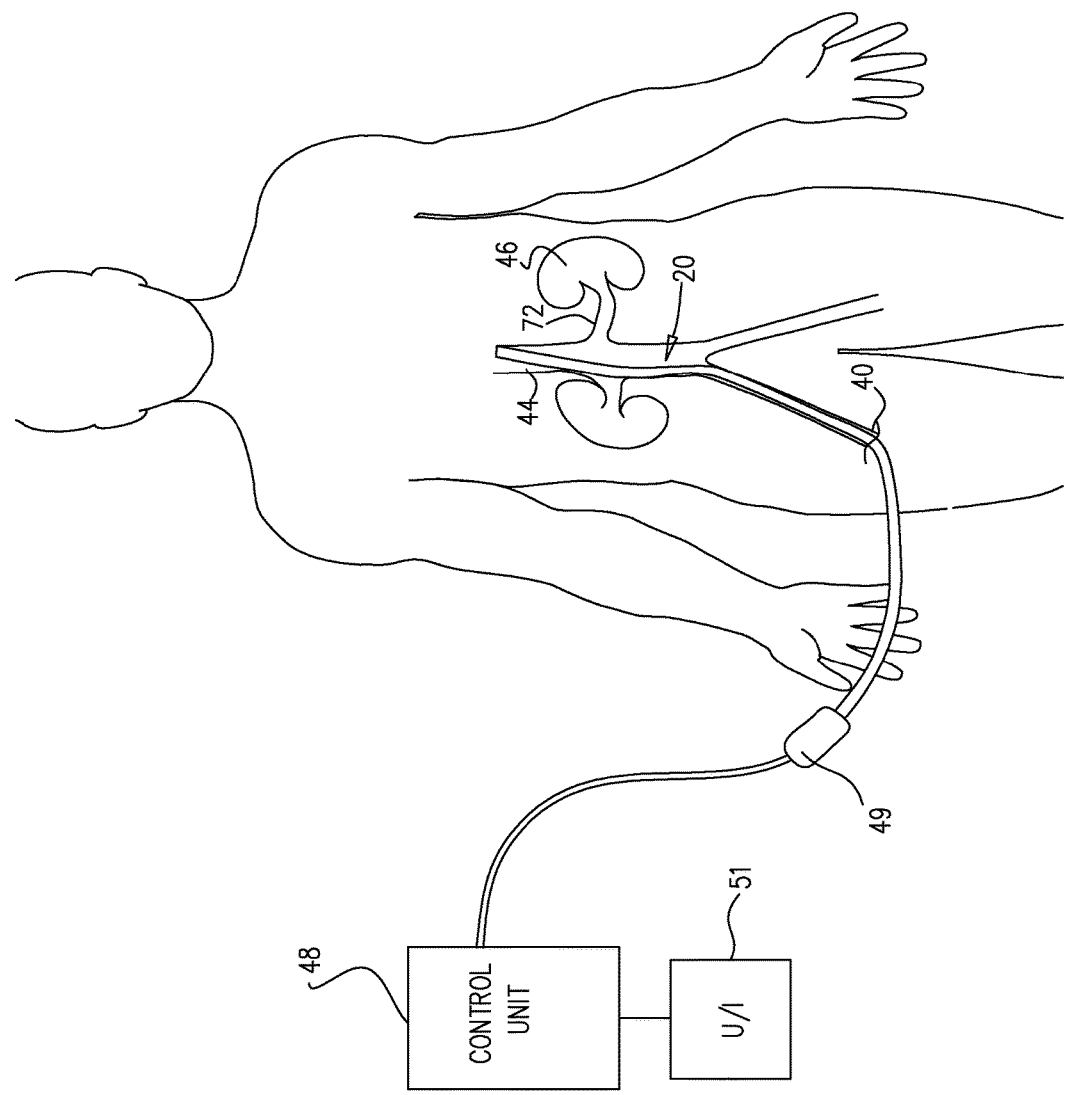
FIGS. 3A-B are schematic illustrations of a catheter being inserted via a vein of a subject's groin, a distal end of the catheter being placed into a renal vein of the subject that is contralateral to the vein of the groin, in accordance with some applications of the present invention.
Figure 3B:
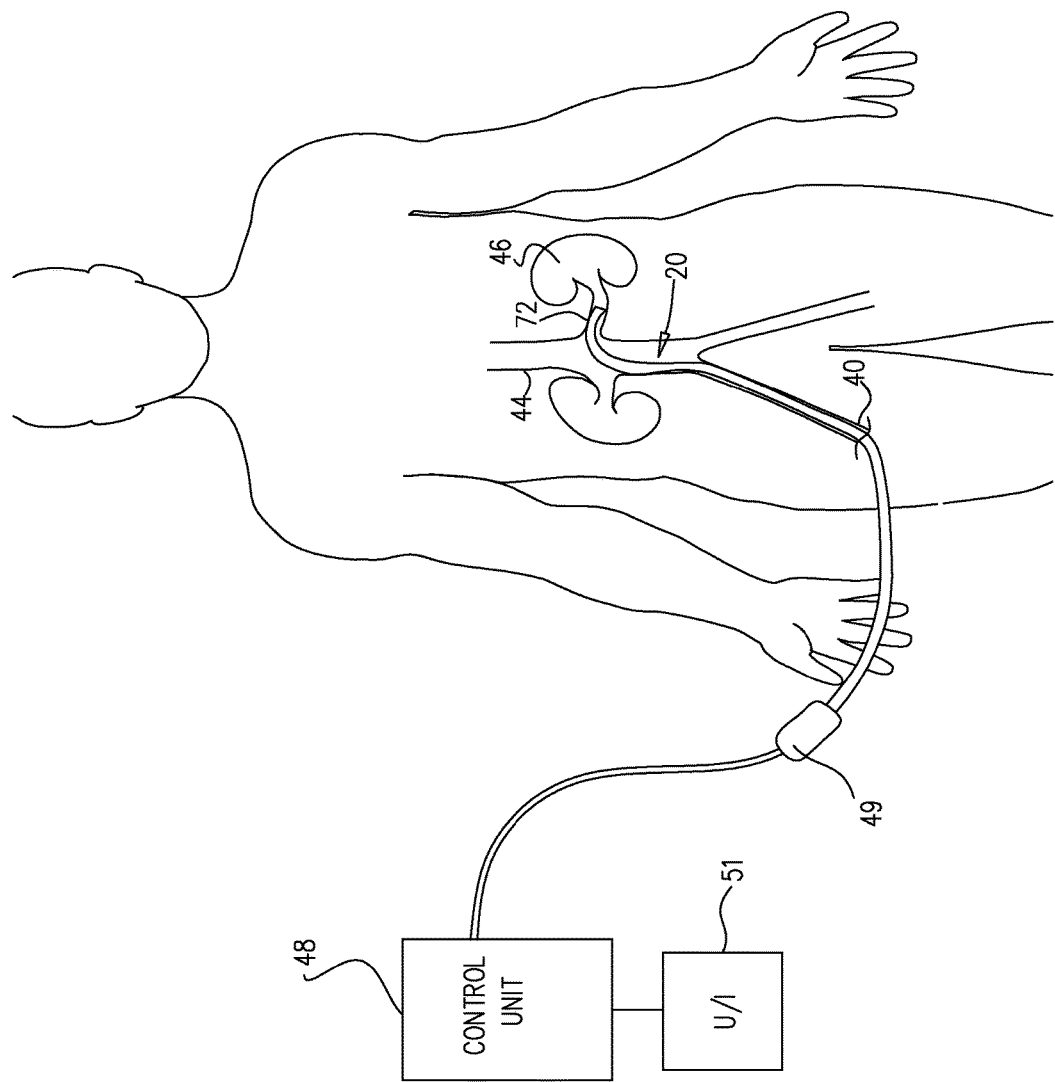

Reference is now made to FIGS. 3A-B, which are schematic illustrations of catheter 20 being inserted via a vein of a subject's groin (right femoral vein 40, in the example shown), a distal end of the catheter being advanced into a renal vein of the subject that is contralateral to the vein of the groin (e.g., left renal vein 72, in the example shown), in accordance with some applications of the present invention.

For some applications, in order to insert the distal end of the catheter into renal vein 72, the distal end of the catheter is first placed into the subject's vena cava 44, downstream of (i.e., distal to) the renal vein. The catheter is inserted such that due to the curvature of the catheter, the distal tip of the catheter pushes against the inner wall of the vena cava on the contralateral side of the vena cava, as shown in FIG. 3A. The catheter is then retracted proximally, such that when the distal tip of the catheter passes the opening to the renal vein, the distal tip of the catheter enters the renal vein. When the distal tip has entered the renal vein, the catheter is then advanced, such that the distal tip of the catheter is disposed inside the renal vein in the vicinity of the subject's kidney 46, as shown in FIG. 3B. As described hereinabove with reference to FIGS. 2A-B, typically, the tip of catheter 20 being atraumatic reduces a likelihood of an injury being caused to the inner wall of the vena cava, during the insertion of the catheter, relative to if the distal tip of the catheter were not atraumatic.

Figure 3C:
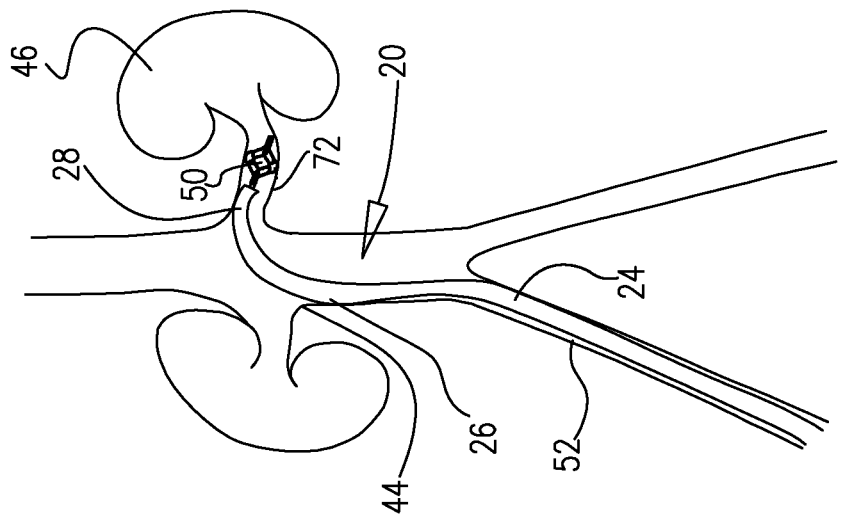
FIGS. 3C-D are schematic illustrations of portions of the catheter, respectively before and after a medical device has been deployed inside the contralateral renal vein, via the distal end of the catheter, in accordance with some applications of the present invention.
Figure 3D:
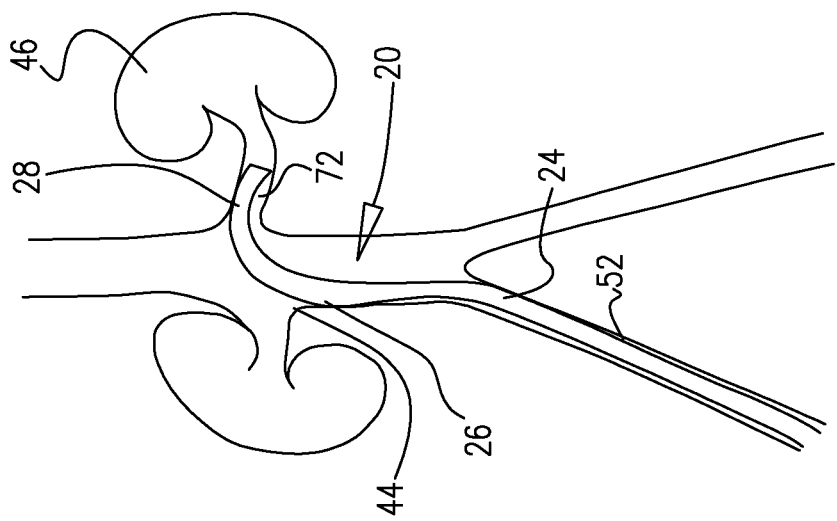

Reference is now made to FIGS. 3C-D, which are schematic illustrations of portions of catheter 20, respectively before and after medical device 50 has been deployed inside renal vein 72, via the distal end of the catheter, in accordance with some applications of the present invention. Typically, during deployment of medical device 50 inside renal vein 72 (i.e., during retraction of catheter 20 from the position shown in FIG. 3C to the position shown in FIG. 3D), second portion 24 of the catheter is configured to stabilize the catheter by contacting an inner wall of iliac vein 52. Further typically, subsequent to the deployment of the medical device inside the renal vein second portion 24 of the catheter is configured to stabilize the catheter by contacting the inner wall of iliac vein 52, as shown in FIG. 3D. As described hereinabove, with reference to FIGS. 2C-D, for some applications, the device is temporarily placed inside the subject's renal vein, in order to provide an acute treatment to the subject. The catheter remains in place inside the subject's vasculature during the treatment, and the second portion of the catheter provides stabilization to the catheter by contacting the inner wall of iliac vein 52, as shown in FIG. 3D. Subsequent to the treatment being terminated, the device is withdrawn from the subject's renal vein via the catheter.

As described hereinabove with reference to FIGS. 2C-D, the length of the second portion of the tube defined by catheter 20 is typically at least twice the length (e.g., at least 3 times the length) of medical device 50. Typically, the second portion is thus configured to contact the inner wall of iliac vein 52 both (a) before the catheter has been retracted such as to release the device from the distal end of the catheter (as shown in FIG. 3C), and (b) subsequent to the catheter having been retracted at least by the length of the device, such as to release the device from the distal end of the catheter (as shown in FIG. 3D).

As described hereinabove, for some applications, medical device 50 is a blood pump that includes a radially-expandable impeller disposed inside a radially-expandable impeller cage, e.g., as described with reference to 12Ai-22Cii of WO 14/141284 to Schwammenthal, which is incorporated herein by reference. For such applications, the length of the cage, measured along the longitudinal axis of the cage, is typically greater than 17 mm, less than 26 mm, and/or between 17 and 26 mm. For some applications, the length of second portion 24 of the tube defined by catheter 20 is at least 30 mm (e.g., at least 50 mm), and/or less than 80 mm (e.g., less than 65 mm).

Typically, during deployment of medical device 50 inside renal vein 72 (i.e., during retraction of catheter 20 from the position shown in FIG. 3C to the position shown in FIG. 3D), third portion 26 of the catheter is configured to stabilize the catheter by contacting an inner wall of the subject's vena cava 44. Further typically, subsequent to the deployment of the medical device inside the renal vein, third portion 26 of the catheter is configured to stabilize the catheter by contacting the inner wall of the vena cava, as shown in FIG. 3D. As described hereinabove, the length of the third portion of the tube defined by catheter 20 is typically at least twice the length (e.g., at least 3 times the length) of medical device 50. Typically, the third portion is thus configured to contact the inner wall of vena cava 44 both (a) before the catheter has been retracted such as to release the device from the distal end of the catheter (as shown in FIG. 3C), and (b) subsequent to the catheter having been retracted at least by the length of the device, such as to release the device from the distal end of the catheter (as shown in FIG. 3D).

As described hereinabove, for some applications, medical device 50 is a blood pump that includes a radially-expandable impeller disposed inside a radially-expandable impeller cage, e.g., as described with reference to 12Ai-22Cii of WO 14/141284 to Schwammenthal, which is incorporated herein by reference. For such applications, the length of the cage, measured along the longitudinal axis of the cage, is typically greater than 17 mm, less than 26 mm, and/or between 17 and 26 mm. For some applications, the length of third portion 26 of the tube defined by catheter 20 is at least 30 mm (e.g., at least 50 mm), and/or less than 80 mm (e.g., less than 65 mm).

For some applications, during at least a portion of the deployment of medical device 50 inside renal vein 72, fourth portion 28 of the catheter is configured to stabilize the catheter by contacting an inner wall of the subject's renal vein. For example, as shown in FIG. 3C, prior to the retraction of catheter 20 such as to deploy device 50, the fourth portion stabilizes the catheter by contacting the inner wall of the renal vein. For some applications, fourth portion 28 of the catheter is configured to stabilize the catheter by contacting an inner wall of the subject's renal vein even after the device has been deployed by the catheter having been retracted proximally, as shown in FIG. 3D.

Figure 3E:
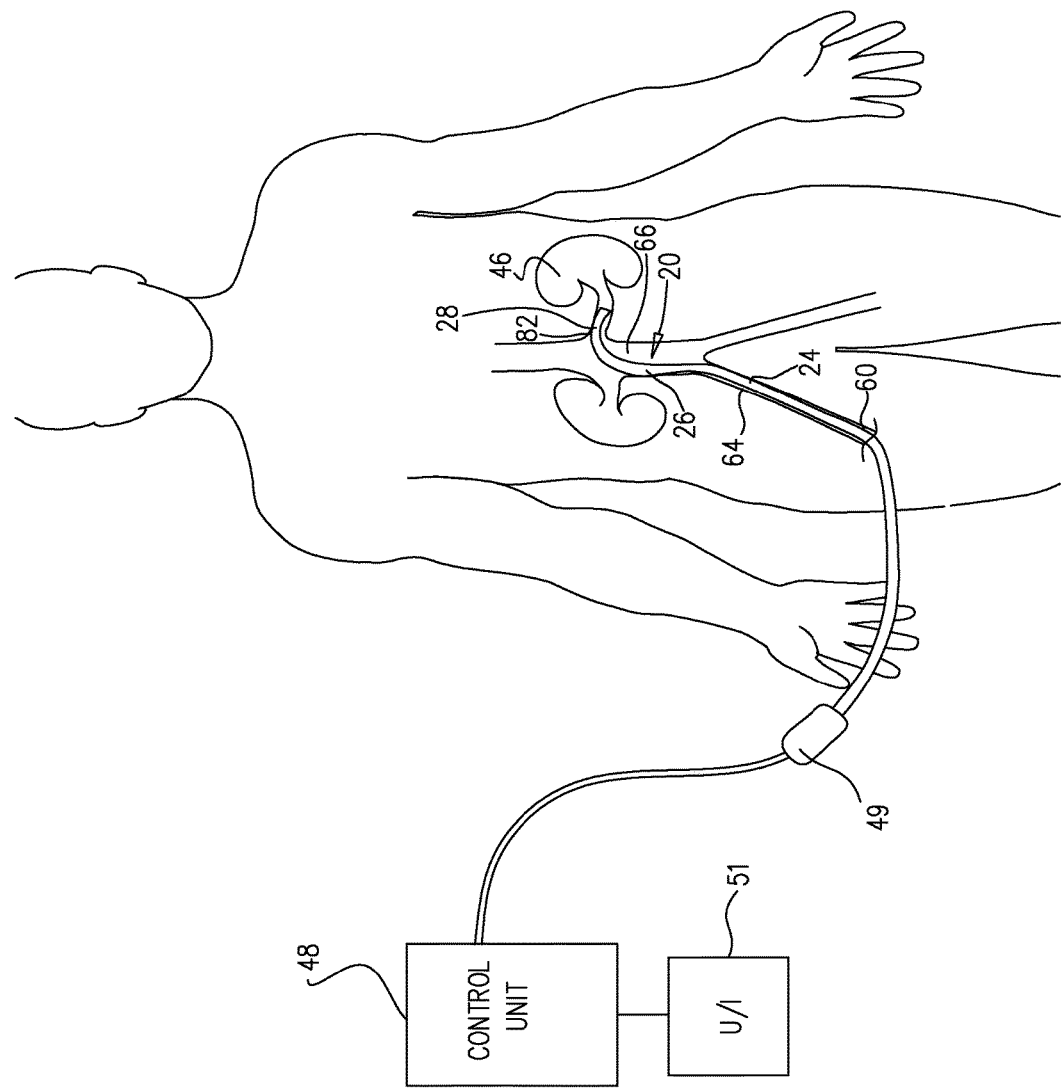
FIG. 3E is a schematic illustration of a catheter that has been inserted, via an artery of a subject's groin, such that a distal end of the catheter is placed into a renal artery of the subject that is contralateral to the artery of the groin, in accordance with some applications of the present invention.

Reference is now made to FIG. 3E, which is a schematic illustration of catheter 20, the catheter having been inserted into the subject's vasculature via an artery of a subject's groin (right femoral artery 60, in the example shown). A distal end of the catheter is advanced into a renal artery of the subject that is contralateral to the artery of the groin (e.g., right renal artery 82, in the example shown). For some applications, generally similar techniques to those described hereinabove with reference to FIGS. 3A-3D are performed on the arterial side of the subject's vasculature, mutatis mutandis. For some applications, when catheter 20 is used on the arterial side of the subject's vasculature, during at least a portion of the procedure (a) second portion 24 of the catheter stabilizes the catheter by contacting an inner wall of an iliac artery 64 of the subject, (b) third portion 26 of the catheter stabilizes the catheter by contacting an inner wall of an aorta 66 of the subject, and (c) fourth portion 28 of the catheter stabilizes the catheter by contacting an inner wall of renal artery 82. Typically, both before and after the catheter is retracted such as to release device 50 inside the renal artery, (a) second portion 24 of the catheter stabilizes the catheter by contacting the inner wall of iliac artery 64, and (b) third portion 26 of the catheter stabilizes the catheter by contacting the inner wall of aorta 66.

It is noted that, in accordance with the above description of catheter 20, the catheter is shaped such that both (a) when the catheter is placed into a renal vessel that is ipsilateral with respect to the vessel of the groin via which the catheter is inserted, and (b) when the catheter is placed into a renal vessel that is ipsilateral with respect to the vessel of the groin via which the catheter is inserted, the catheter is stabilized by portions of the catheter contacting inner walls of the blood vessels of the subject at at least two points. Typically, the second portion of the catheter stabilizes the catheter by contacting an inner wall of an iliac vessel of the subject, and the third portion stabilizes the catheter by contacting an inner of the vena cava or the aorta of the subject. Further typically, the catheter is stabilized by portions of the catheter contacting inner walls of the blood vessels of the subject at the at least two points (a) before the catheter is retracted such as to release the device from the distal end of the catheter, and (b) subsequent to the catheter having been retracted such as to release the device from the distal end of the catheter.

It is noted that, for some applications, catheter 20 is used for the insertion of a medical device therethrough that provides a therapy (e.g., renal denervation) to a renal vessel (e.g., a renal artery or a renal vein). Subsequent to providing the therapy, the device is withdrawn from the renal vessel via the catheter. Catheter 20 provides stabilization during the advancement of the device, during the withdrawal of the device, and/or during the provision of the therapy by (a) second portion 24 of the catheter stabilizing the catheter by contacting an inner wall of an iliac vessel of the subject, (b) third portion 26 of the catheter stabilizing the catheter by contacting an inner wall of vena cava 44 or aorta 66 of the subject, and, optionally, (c) fourth portion 28 of the catheter stabilizing the catheter by contacting an inner wall of the renal vessel, in accordance with the techniques described hereinabove.

Although catheter 20 is described hereinabove as being inserted via a femoral blood vessel, for some applications, catheter 20 is inserted through a different peripheral vessel in the subject's groin, e.g., the iliofemoral vein. Alternatively or additionally, the catheter is inserted via a vein of the arm (e.g., a brachial, or antecubital vein), the chest (e.g., the subclavian vein), or the neck (e.g., the jugular vein). For some applications, catheter 20 is inserted into the hepatic vein.

In general, in the specification and in the claims of the present application, the term "proximal" and related terms, when used with reference to a device or a portion thereof, should be interpreted to mean an end of the device or the portion thereof that, when inserted into a subject's body, is typically closer to a location through which the device is inserted into the subject's body. The term "distal" and related terms, when used with reference to a device or a portion thereof, should be interpreted to mean an end of the device or the portion thereof that, when inserted into a subject's body, is typically further from the location through which the device is inserted into the subject's body.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
  inserting a catheter into a body of a subject via a vein of a groin of the subject, and
  advancing the catheter distally such that:
    a distal end of the catheter is disposed inside a renal vein of the subject, and
    respective stabilizing portions of the catheter stabilize the catheter by being in contact with inner walls of, respectively, an iliac vein of the subject, and a vena cava of the subject; and
  subsequently, deploying a medical device inside the renal vein by retracting the distal end of the catheter, such that the distal end of the catheter is in a retracted state, in which the respective stabilizing portions of the catheter still stabilize the catheter by being in contact with the inner walls of, respectively, the subject's iliac vein and the subject's vena cava.

2. The method according to claim 1, wherein advancing the catheter distally comprises advancing the catheter distally such that a further stabilizing portion of the catheter stabilizes the catheter by being in contact with an inner wall of the renal vein.

3. The method according to claim 1, wherein retracting the distal end of the catheter comprises retracting the distal end of the catheter, such that while the distal end of the catheter is in its retracted state, a further stabilizing portion of the catheter stabilizes the catheter by being in contact with an inner wall of the renal vein.

4. The method according to claim 1, wherein advancing the catheter distally such that the distal end of the catheter is disposed inside the subject's renal vein comprises advancing the catheter distally such that the distal end of the catheter is disposed inside a renal vein of the subject that is contralateral to the vein of the subject's groin via which the catheter is inserted.

5. The method according to claim 1, wherein advancing the catheter distally such that the distal end of the catheter is disposed inside the subject's renal vein comprises advancing the catheter distally such that the distal end of the catheter is disposed inside a renal vein of the subject that is ipsilateral to the vein of the subject's groin via which the catheter is inserted.

6. The method according to claim 1, further comprising operating the medical device, inside the renal vein, while the catheter is disposed inside a body of the subject in its retracted state, such that the catheter supports the medical device during its operation.

7. The method according to claim 6, wherein deploying the device comprises deploying a radially-expandable impeller that is disposed inside a radially-expandable impeller cage, and wherein operating the medical device comprises rotating the impeller.

* * * * *